(12) United States Patent
Yoshimura et al.

(10) Patent No.: US 7,692,018 B2
(45) Date of Patent: Apr. 6, 2010

(54) PROCESS FOR PRODUCING HIGH PURITY 3,5-DIHYDROXY-6-HEPTENOIC ACID DERIVATIVE

(75) Inventors: Yuji Yoshimura, Onoda (JP); Masami Yasukawa, Sodegaura (JP); Syuji Morikiyo, Onoda (JP); Yasutaka Takada, Funabashi (JP); Hiroo Matsumoto, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 1054 days.

(21) Appl. No.: 10/568,347

(22) PCT Filed: Sep. 22, 2004

(86) PCT No.: PCT/JP2004/014289

§ 371 (c)(1),
(2), (4) Date: Feb. 14, 2006

(87) PCT Pub. No.: WO2005/033083

PCT Pub. Date: Apr. 14, 2005

(65) Prior Publication Data

US 2006/0229451 A1    Oct. 12, 2006

(30) Foreign Application Priority Data

Oct. 3, 2003    (JP) .............................. 2003-346019

(51) Int. Cl.
*C07D 215/12* (2006.01)
(52) U.S. Cl. ...................................... 546/174
(58) Field of Classification Search .................. 546/174
See application file for complete search history.

(56) References Cited

U.S. PATENT DOCUMENTS 5,011,930 A    4/1991    Fujikawa et al.

FOREIGN PATENT DOCUMENTS

| EP | 0747 341 | * | 2/1995 |
| EP | 0 747 341 | | 12/1996 |
| EP | 1334967 | * | 10/2001 |
| EP | 1 334 967 | | 8/2003 |
| JP | 0 304 063 | | 2/1989 |
| WO | 2004/026838 | | 4/2004 |

* cited by examiner

Primary Examiner—D. Margaret Seaman
Assistant Examiner—Nizal S Chandrakumar
(74) Attorney, Agent, or Firm—Oblon, Spivak, McClelland, Maier & Neustadt, L.L.P.

(57) ABSTRACT

A process for producing a high purity 3,5-dihydroxy6-heptenoic acid derivative by controlling the content of impurities such as denatured substances, is provided. When a 3,5-dihydroxy-6-heptenoic acid derivative is produced by a process which comprises a step of contacting the 3,5-dihydroxy-6-heptenoic acid derivative of the formula (1) wherein R is a $C_{1-4}$ alkyl group, with a $C_{1-4}$ lower alcohol-containing solvent, an alcohol containing solvent having its content of an oxidizing substance lowered, is used to at most 0.05 molar equivalent to a 3,5-dihydroxy-6-heptenoic acid derivative, to suppress impurities contained in the 3,5-dihydroxy-6heptenoic acid derivative.

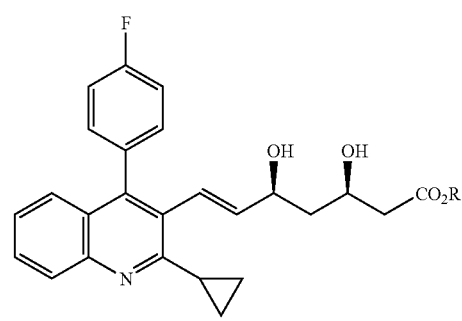

(1)

7 Claims, No Drawings

PROCESS FOR PRODUCING HIGH PURITY 3,5-DIHYDROXY-6-HEPTENOIC ACID DERIVATIVE

TECHNICAL FIELD

The present invention relates to a process for producing a high purity 3,5-dihydroxy-6-heptenoic acid derivative having a very small content of impurities such as denatured substances. More particularly, it relates to a process for producing a high purity 3,5-dihydroxy-6-heptenoic acid derivative which is useful as a medicinal intermediate such as ethyl(3R,5S)-7-[2-cyclopropyl-4-(4-fluorophenyl)quinolin-3-yl]-3,5-dihydroxy-6-heptenoate (hereinafter referred to as (3R,5S) DOLE), methyl (3R,5S)-7-[2-cyclopropyl-4-(4-fluorophenyl)quinolin-3-yl]-3,5-dihydroxy-6-heptenoate (hereinafter referred to as (3R,5S) DOLM).

BACKGROUND ART

A 3,5-dihydroxy-6-heptenoic acid derivative represented by (3R,5S) DOLE or (3R,5S) DOLM is known to be useful as an intermediate for a hyperlipemia preventive or curative medicine, or for a medicine for lowering cholesterol (HMG-CoA reductase inhibitor) (JP-A-1-279866, EP-A-304063, U.S. Pat. No. 5,011,930). Such a 3,5-dihydroxy-6-heptenoic acid derivative is produced as a racemic modification as it has an asymmetric carbon. It is known that an optically active isomer can be produced by optical resolution of the racemic modification by liquid chromatography employing an optical isomer separation HPLC column. (WO95/23125)

DISCLOSURE OF THE INVENTION

In optical resolution of a 3,5-dihydroxy-6-heptenoic acid derivative such as (3R,5S) DOLE or a (3R,5S) DOLM by means of an optical isomer separation column (such as CHIRALCEL OF), as an eluent, an alcohol-containing solvent, for example, a mixed solvent of an alcohol with a hydrocarbon (for example, a mixed solvent of n-hexane/isopropanol) is usually used. A fraction of the 3,5-dihydroxy-6-heptenoic acid derivative eluted in such a solvent is collected, and the solvent is distilled off. The obtained alcohol solution of the 3,5-dihydroxy-6-heptenoic acid derivative is further subjected to solvent exchange with a solvent for recrystallization such as a hydrocarbon or a hydrocarbon partially containing an alcohol, followed by crystallization, whereby a pure 3,5-dihydroxy-6-heptenoic acid derivative is obtainable as crystals.

However, with the 3,5-dihydroxy-6-heptenoic acid derivative produced by such a process, a phenomenon of formation of denatured substances may sometimes be observed during its production or storage. A 3,5-dihydroxy-6-heptenoic acid derivative of the formula (1) is converted to a base material for medicine by converting it to a calcium salt after hydrolysis. During the process, its denatured substances tend to color a reaction solution strongly, and they will ultimately color also the medicinal base material. Formation of such impurities occurs even when one having a high purity made of the highest grade chemicals is used as the mixed solvent of a hydrocarbon and an alcohol, to be used in the production process. The content of such denatured substances is very small with ppm order in the 3,5-dihydroxy-6-heptenoic acid derivative to be produced. However, the desired product is to be used as an intermediate for medicines, and therefore, it is necessary to lower the impurities as far as possible.

It is an object of the present invention to provide a novel process capable of producing a high purity 3,5-dihydroxy-6-heptenoic acid derivative which requires no particular purification process after its production, by significantly suppressing the content of the very small amount of impurities such as denatured substances in the desired product in the case of producing a 3,5-dihydroxy-6-heptenoic acid derivative through liquid chromatography employing an optical isomer separation column.

As a result of their extensive study to accomplish the above object, the present inventors have found that formation of the very small amount of impurities such as denatured substances in the 3,5-dihydroxy-6-heptenoic acid derivative as the desired product is caused by an alcohol-containing solvent which is employed e.g. in the process of liquid chromatography employing an optical isomer separation column.

Namely, according to the study by the present inventors, it has been found that, as shown in Example 1 given hereinafter, when an alcohol as the solvent which was employed in the process for producing a 3,5-dihydroxy-6-heptenoic acid derivative, was distilled and concentrated, an oxidizing substance was found therein. And, stability of the 3,5-dihydroxy-6-heptenoic acid derivative as the desired product was investigated in alcohol solvents, which contained the oxidizing substance in various ratios, whereby it has been found that as shown Example 2 given hereinafter, by lowering the content of the oxidizing substance in the alcohol-containing solvent as far as possible, the amount of denatured substances formed in the desired product can be suppressed. Particularly, it has been found that by controlling the amount of the oxidizing substance in the alcohol-containing solvent to at most 0.05 molar equivalent to the 3,5-dihydroxy-6-heptenoic acid derivative, the content of impurities in the desired product can be lowered to a level of not higher than the usually allowable amount.

The present invention has been accomplished based on such a novel finding, and is characterized by the followings:

(1) A process for producing a 3,5-dihydroxy-6-heptenoic acid derivative, which comprises a step of contacting a 3,5-dihydroxy-6-heptenoic acid derivative of the formula (1):

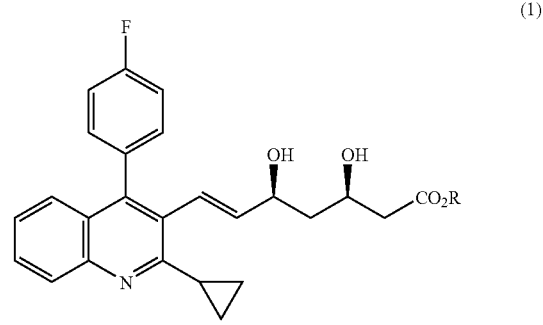

(1)

wherein R is a $C_{1-4}$ alkyl group, with a $C_{1-4}$ lower alcohol-containing solvent, characterized in that an alcohol-containing solvent having its content of an oxidizing substance lowered as far as possible, is used to suppress the amount of impurities which are contained in the 3,5-dihydroxy-6-heptenoic acid derivative.

(2) The process according to above (1), wherein the step of contacting with the alcohol-containing solvent is a step of contacting with the solvent as an eluent for liquid chromatography employing an optical isomer separation column for optical resolution of the 3,5-dihydroxy-6-heptenoic acid derivative of the formula (1).

(3) The process according to above (1) or (2), wherein the content of the oxidizing substance in the alcohol-containing solvent is adjusted to at most 0.05 molar equivalent to the 3,5-dihydroxy-6-heptenoic acid derivative of the formula (1).

(4) The process according to above (1), (2) or (3), wherein R in the formula (1) is a methyl group or an ethyl group.

(5) The process according to any one of above (1) to (4), wherein the alcohol in the alcohol-containing solvent is methanol, ethanol or isopropanol.

(6) The process according to any one of above (1) to (4), wherein the alcohol in the alcohol-containing solvent having the oxidizing substance adjusted to be at most 0.05 molar equivalent to the 3,5-dihydroxy-6-heptenoic acid derivative of the formula (1), is either one obtained by distillation of raw material alcohol or one having raw material alcohol treated with a reducing agent.

According to the present invention, formation of the very small amount of impurities such as denatured substances in the 3,5-dihydroxy-6-heptenoic acid derivative as the desired product can be significantly suppressed, and a high purity 3,5-dihydroxy-6-heptenoic acid derivative can be obtained without performing cumbersome purification treatment for removing the very small amount of impurities after its production. This is extremely meaningful in that the product is to be employed as an intermediate for medicines where even an extremely small amount of impurities may not be allowed.

The reason why the impurities in the desired material can be significantly suppressed by the present invention, is not necessarily clearly understood, but it may be explained as follows:

The alcohol in the alcohol-containing solvent used in the process is basically not so stable. When the alcohol is temporally exposed to a high temperature, a part of it degrades into an oxidizing substance, which is considered to be included in the solvent. The oxidizing substance contained in the alcohol, even in a very small amount, is significant in the step of e.g. liquid chromatography in the production of the desired product of the present invention, in that the 3,5-dihydroxy-6-heptenoic acid derivative as the desired product, will be in contact with the alcohol-containing solvent for a long time of from a few hours to a few days in the operation of adsorption/desorption and during the subsequent transition period for the next treatment.

It is considered that through contact with an alcohol-containing solvent for such a long-time, a part of the desired product is oxidized by an oxidizing substance in the alcohol-containing solvent, and the oxidized is contained as impurities in the desired product. This is supported to some extent by the fact that denatured substances contained in the desired product are mainly ketones formed by oxidation of hydroxyl groups of the 3,5-dihydroxy-6-heptenoic acid derivative.

BEST MODE FOR CARRYING OUT THE INVENTION

The 3,5-dihydroxy-6-heptenoic acid derivative to be produced by the present invention is represented by the following formula (1).

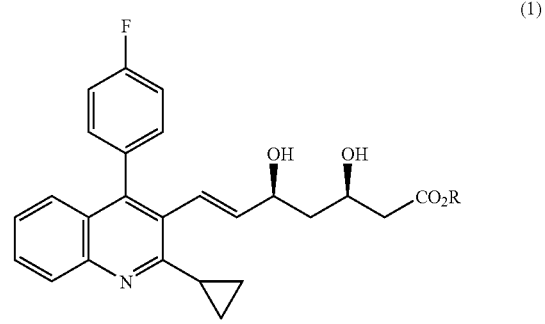

In the formula (1), R is a $C_{1-4}$ alkyl group, preferably a methyl group or an ethyl group. The representative compounds are, for example, ethyl(3R,5S)-7-[2-cyclopropyl-4-(4-fluorophenyl) quinolin-3-yl]-3,5-dihydroxy-6-heptenoate ((3R,5S) DOLE), and methyl (3R,5S)-7-[2-cyclopropyl-4-(4-fluorophenyl) quinolin-3-yl]-3,5-dihydroxy-6-heptenoate ((3R,5S) DOLM). These substances are useful as intermediates for hyperlipemia preventive or curative medicines, or for medicines for lowering cholesterol (HMG-CoA reductase inhibitor).

Such a 3,5-dihydroxy-6-heptenoic acid derivative has an asymmetric carbon, and, a compound synthesized by a known process is a racemic modification. In the present invention, as mentioned above, an alcohol-containing solvent is employed in a process for obtaining an optically active isomer by optical resolution of the racemic modification by liquid chromatography employing an optical isomer separation HPLC column (e.g. "CHIRALCEL OF" manufactured by Daicel Chemical Industries, Ltd), and a contacting treatment with the alcohol-solvent is carried out.

The alcohol in the alcohol-containing solvent is usually a $C_{1-4}$ lower alcohol, and it may, for example, be methanol, ethanol, propanol or isopropanol. In the present invention, isopropanol is particularly effective. The alcohol-containing solvent may be employed as an alcohol itself depending on a case, but it is usually used as a solvent mixture with other solvents. As an eluent in the above-mentioned liquid chromatography, a solvent mixture with a hydrocarbon is employed. The solvent mixture in this case is, preferably, a solvent mixture containing a hydrocarbon such as hexane, heptane or cyclohexane, preferably in an amount of from 500 to 50 parts by mass per 100 parts by mass of the alcohol.

In the present invention, as such an alcohol-containing solvent, one having the content of an oxidizing substance in the solvent lowered as far as possible, is employed. It is particularly preferred that the content of the oxidizing substance in the alcohol-containing solvent is adjusted to at most 0.05 molar equivalent to the 3,5-dihydroxy-6-heptenoic acid derivative. It is preferred to maintain this amount of the oxidizing substance throughout the entire process in which the 3,5-dihydroxy-6-heptenoic acid derivative as the desired product is in contact with the alcohol-containing solvent. In the present invention, the oxidizing substance contained in the alcohol-containing solvent is one obtained by an iodine titration method according to the following formula. For example, it is obtained by taking an exact amount of 20 mL of a sample (the weight is also measured), diluting it with 50 mL of water, adding 2 g of potassium iodine (KI) and 10 mL of an aqueous acetic acid solution thereto, sealing it hermetically, and then after leaving it to stand still in a dark room for at least 15 min, titrating it with 0.01 mol/L of an aqueous sodium thiosulfate solution by means of a potentiometric automatic titration method.

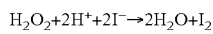

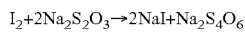

In the present invention, if the content of the oxidizing substance in the alcohol-containing solvent is larger than 0.05 molar equivalent to the 3,5-dihydroxy-6-heptenoic acid derivative of the formula (1), the amount of impurities such as denatured substances included in the 3,5-dihydroxy-6-heptenoic acid derivative produced cannot be reduced to such a low level that satisfies at most 1000 ppm which is usually deemed to be free from problem. In the present invention, the amount of impurities such as denatured substances in the desired product, can be dramatically reduced by bringing the content of the oxidizing substance in the alcohol-containing solvent to be preferably at most 0.05 molar equivalent, particularly preferably, at most 0.02 molar equivalent, to the 3,5-dihydroxy-6-heptenoic acid derivative. Here, the molar equivalent of the oxidizing substance is calculated as converted to hydrogen peroxide.

As means to obtain an alcohol-containing solvent having the content of the oxidizing substance lowered, various methods may be employed, and such means are not particularly limited in the present invention. However, the following methods may preferably be employed.

One of them is a method of employing a solvent which contains an alcohol having a residue removed by distillation. As shown in the after-mentioned Example 1, it is possible to certainly reduce the amount of the contained oxidizing substance by repeating distillation of the raw material alcohol. As the distillation method, a common distillation method such as atmospheric distillation, reduced-pressure distillation or azeotropic distillation may, for example be employed.

Another method is a method of employing a solvent which contains an alcohol wherein an oxidizing substance is reduced by addition of a reducing agent. As such a reducing substance, hydroquinone or sodium thiosulfate is preferred in the present invention. When such a reducing agent is used, it is possible to suppress denaturation by lactonization of the 3,5-dihydroxy-6-heptenoic acid derivative such as (3R,5S) DOLE or (3R,5S) DOLM, which is likely to take place when other reducing agents are used. The reducing agent is used preferably in an amount within a range of from 0.5 to 10 equivalent, particularly preferably within a range of from 1 to 5 equivalent, to the amount of the oxidizing substance included in the raw material alcohol. The temperature for treatment with the reducing agent is preferably within a range of from 10 to 60° C., particularly preferably within a range of from 20 to 40° C.

Among the above two processes of obtaining an alcohol having the content of the oxidizing substance lowered, the former process is preferred in the present invention, because it can certainly lower the content of the oxidizing substance, and as compared with the latter process, the obtainable alcohol having the content of the oxidizing substance lowered does not include an excessive reducing agent or impurities such as reaction products or the reducing agent and the oxidizing substance.

A known process as disclosed in WO95/23125 or WO02/30903 may be employed for the process of obtaining an optically active isomer by optical resolution of the racemic modification by liquid chromatography treatment such as a batch method or a simulated moving bed method employing an optical isomer separation HPLC column by using an alcohol-containing solvent having the content of the oxidizing substance lowered.

The present invention will now be described in further detail with reference to Examples. However, it should be understood that the present invention is by no means restricted to such specific Examples.

EXAMPLE 1

A commercially available highest-grade isopropanol was concentrated 160 times by distillation under atmospheric pressure to obtain a concentrated liquid and a distillate. Distillation to concentrate the obtained distillate 160 times again, was repeated for 3 more times, and the amount ($mgH_2O_2/g$) of an oxidizing substance contained in each isopropanol liquid obtained was measured. The results are shown in Table 1.

TABLE 1

| Type of liquid | Content of the oxidizing substance |
| --- | --- |
| Commercially available isopropanol | Not detected |
| Concentrated liquid obtained by first distillation | 0.381 |
| Concentrated liquid obtained by second distillation | 0.114 |
| Concentrated liquid obtained by third distillation | 0.079 |
| Distillate obtained by third distillation | Not detected |

Further, 240 mg of (3R,5S) DOLE was dissolved in 10 mL of each liquid as identified in Table 1 and left to stand in a constant temperature bath at 40° C. for 4 days, whereby the amount of denatured substances in (3R,5S) DOLE was measured and shown in Table 2 by percentage in the total substances including (3R,5S) DOLE.

The impurities contained in (3R,5S) DOLE were analyzed by nuclear magnetic resonance and mass spectrum, whereby it was confirmed that the impurities were mainly ketones. The analysis of the content of impurities was carried out by using 4.6 IDx 250 mmL L-ColumnODS which was packed with octadecyl group chemically bonded type silica packing (Foundation of Chemicals Evaluation and Research Institute), an ethanol/tetra/hydrofuran/0.01 M ammonium acetate solution (45:3:52, V/V/V), 1.0 mL/min, 40° C., wave length 254 nm.

TABLE 2

| Time | Concentrated liquid obtained by first distillation | Concentrated liquid obtained by second distillation | Concentrated liquid obtained by third distillation | Distillate obtained by third distillation |
| --- | --- | --- | --- | --- |
| Start | 0.000% | 0.000% | 0.000% | 0.000% |
| One day later | 0.016% | 0.000% | 0.000% | 0.000% |
| Two days later | 0.031% | 0.000% | 0.000% | 0.000% |
| Three days later | 0.049% | 0.000% | 0.000% | 0.000% |
| Four days later | 0.076% | 0.000% | 0.000% | 0.000% |

As is evident from Table 2, the (3R,5S) DOLE that contacted for 4 days with the concentrated liquid obtained by the first distillation i.e. the isopropanol liquid, containing an oxidizing substance in high 5 concentration, contains impurities, and their content increases with time. On the other hand, it is evident that the (3R,5S) DOLE that contacted with the concentrated liquid or distillate obtained by the second or subsequent distillation i.e. isopropanol liquid without containing an oxidizing substance in high concentration, contains no denatured substance even after the contact for 4 days.

EXAMPLE 2

500 mg of (3R,5S) DOLE was dissolved in 0.64 ml (equivalent to 0.5 g) of a commercially available highest-grade isopropanol (IPA). On the other hand, 1.0035 g of a 9.26 mmol/g $H_2O_2$ aqueous solution was weighed and adjusted to 10 ml with the same commercially available highest-grade isopropanol as mentioned above, to prepare 0.929 mmol/g $H_2O_2$-IPA.

This $H_2O_2$—IPA solution was added to the above IPA solution of (3R,5S) DOLE, so that the amount of $H_2O_2$ in the isopropanol would be 10 μl, 20 μl, 50 μl and 100 μl, respectively. The obtained liquids were left to stand for 4 days in the constant temperature bath at 40° C. under light shielding condition, and the amounts of denatured substances (ppm) formed, were detected in the same manner as in Example 1. The results are shown in Table 3. The $H_2O_2$ content in IPA in Table 3 is the molar equivalent of $H_2O_2$ per (3R,5S) DOLE.

TABLE 3

| | Amount added to the (3R, 5S) DOLE solution | | | | |
|---|---|---|---|---|---|
| | No addition | 10 μl | 20 μl | 50 μl | 100 μl |
| $H_2O_2$ Content in IPA | 0 | 0.0084 | 0.017 | 0.042 | 0.084 |
| Start | 0 | 0 | 20 | 0 | 0 |
| One day later | 0 | 40 | 60 | 140 | 180 |
| Two days later | 0 | 60 | 120 | 320 | 420 |
| Three days later | 0 | 70 | 170 | 480 | 640 |
| Four days later | 0 | 110 | 270 | 830 | 1140 |

As shown in Table 3, as the peroxide concentration in isopropanol increases, the content of impurities in (3R,5S) DOLE increases. However, it is evident that if the content of peroxide in isopropanol is maintained to be 0.05 molar equivalent, the content of impurities in (3R,5S) DOLE can be suppressed to be at most 1000 ppm which is usually allowable.

EXAMPLE 3

Reducing Agent: Hydroquinone 240 mg of (3R,5S) DOLE was dissolved in 9 ml of commercially available isopropanol. For accelerated test, to the solution, 0.5 ml (0.09 eq.) of an isopropanol solution containing 0.097 mmol/ml of a $H_2O_2$ aqueous solution was added to obtain a liquid (blank liquid), which was left to stand for 4 days in a constant temperature bath at 40° C.

On the other hand, to the above blank solution, 1 ml of a 0.0272 mmol/ml hydroquinone-isopropanol solution was further added to obtain a liquid (hydroquinone-added liquid), which was left to stand for 4 days in a constant temperature bath at 40° C. in the same manner as above.

In the each of above tests, the amount of denatured substances contained in the obtained (3R,5S) DOLE was measured and shown in Table 4.

TABLE 4

| Time | Blank liquid | Hydroquinone-added liquid |
|---|---|---|
| Start | 0.000% | 0.000% |
| One day later | 0.003% | 0.002% |
| Two days later | 0.004% | 0.000% |
| Three days later | 0.005% | 0.000% |
| Four days later | 0.007% | 0.000% |

EXAMPLE 4

Reducing Agent: Sodium Thiosulfate 240 mg of (3R,5S) DOLE was dissolved in 9 mL of commercially available isopropanol. For accelerated stability test, to the solution, 0.5 ml (0.09 eq.) of an isopropanol solution containing 0.097 mmol/ml of a $H_2O_2$ aqueous solution was added to obtain a liquid (blank liquid), which was left to stand for 4 days in a constant temperature bath at 40° C. (blank).

On the other hand, to the above blank solution, 1 ml of a 0.0265 mmol/ml sodium thiosulfate aqueous solution was further added to obtain a liquid (sodium thiosulfate-added liquid), which was left to stand for 4 days in a constant temperature bath at 40° C., in the same manner as described above.

In each of the above tests, the amount of denatured substances contained in the obtained (3R,5S) DOLE was measured and shown in Table 5.

TABLE 5

| Time | Blank liquid | Sodium thiosulfate-added liquid |
|---|---|---|
| Start | 0.000% | 0.000% |
| One day later | 0.003% | 0.000% |
| Two days later | 0.004% | 0.000% |
| Three days later | 0.005% | 0.000% |
| Four days later | 0.007% | 0.000% |

The invention claimed is:

1. A process for producing a high purity 3,5-dihydroxy-6-heptenoic acid derivative according to the following general formula (1):

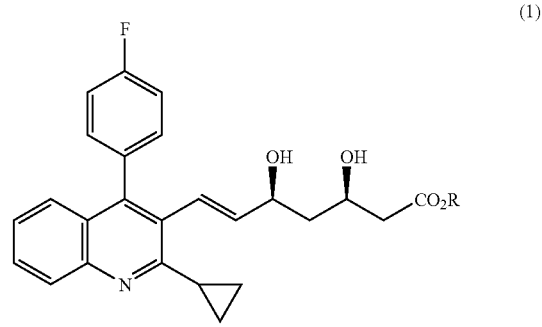

(1)

wherein R represents a $C_1$-$C_4$ alkyl group,
wherein said process comprises liquid chromatography of the 3,5-dihydroxy-6-heptenoic acid derivative of formula (1) with a $C_1$-$C_4$ alcohol-containing solvent, wherein the $C_1$-$C_4$ alcohol-containing solvent has its content of an oxidizing substance adjusted to <0.05 molar equivalent to the 3,5-dihydroxy-6-heptenoic acid derivative of formula (1) by conducting distillation or treatment with a reducing agent.

2. The process according to claim 1, wherein said liquid chromatography employs an optical isomer separation column for optical resolution of the 3,5-dihydroxy-6-heptenoic acid derivative of formula (1).

3. The process according to claim 1, wherein R represents a methyl group or an ethyl group.

4. The process according to claim 1, wherein the $C_1$-$C_4$ alcohol-containing solvent comprises a $C_1$-$C_4$ alcohol selected from the group consisting of methanol, ethanol, propanol and isopropanol.

5. The process according to claim 1, wherein the $C_1$-$C_4$ alcohol-containing solvent comprises a $C_1$-$C_4$ alcohol and a hydrocarbon.

6. The process according to claim 5, wherein the hydrocarbon is selected from the group consisting of hexane, heptane and cyclohexane.

7. The process according to claim 1, wherein the $C_1$-$C_4$ alcohol-containing solvent has its content of an oxidizing substance adjusted to <0.05 molar equivalent to the 3,5-dihydroxy-6-heptenoic acid derivative of formula (1) by conducting distillation of a raw material alcohol.

* * * * *